US011974890B2

(12) United States Patent
Junger et al.

(10) Patent No.: US 11,974,890 B2
(45) Date of Patent: May 7, 2024

(54) AUTHENTICATION SYSTEMS AND METHODS FOR AN EXCIMER LASER SYSTEM

(71) Applicant: Elios Vision, Inc., Los Angeles, CA (US)

(72) Inventors: Johannes Junger, Gilching (DE); Markus Enders, Munich (DE)

(73) Assignee: Elios Vision Inc., Los Angeles, CA (US)

( * ) Notice: Subject to any disclaimer, the term of this patent is extended or adjusted under 35 U.S.C. 154(b) by 166 days.

(21) Appl. No.: 17/363,656

(22) Filed: Jun. 30, 2021

(65) Prior Publication Data

US 2022/0022997 A1    Jan. 27, 2022

Related U.S. Application Data

(63) Continuation of application No. 16/389,346, filed on Apr. 19, 2019, now Pat. No. 11,076,933.

(51) Int. Cl.
*A61B 90/98* (2016.01)
*A61F 9/008* (2006.01)
*G06K 19/077* (2006.01)

(52) U.S. Cl.
CPC .......... *A61B 90/98* (2016.02); *A61F 9/00814* (2013.01); *G06K 19/077* (2013.01)

(58) Field of Classification Search
CPC .... A61B 90/98; A61F 9/00814; G06K 19/077
USPC ........................................................ 235/375
See application file for complete search history.

(56) References Cited

U.S. PATENT DOCUMENTS

| | | | |
|---|---|---|---|
| 4,607,622 A | 8/1986 | Fritch et al. |
| 4,846,172 A | 7/1989 | Berlin |
| 4,862,888 A | 9/1989 | Yessik |
| 5,281,241 A | 1/1994 | Patel |
| 5,323,766 A | 6/1994 | Uram |
| 5,738,677 A | 4/1998 | Colvard et al. |
| 5,755,716 A | 5/1998 | Garito et al. |
| 5,865,831 A | 2/1999 | Cozean et al. |
| 6,197,056 B1 | 3/2001 | Schachar |
| 6,283,974 B1 | 9/2001 | Alexander |
| 6,743,221 B1 | 6/2004 | Hobart et al. |

(Continued)

FOREIGN PATENT DOCUMENTS

| | | |
|---|---|---|
| DE | 19920615 A1 | 12/2000 |
| DE | 10023176 A1 | 11/2001 |

(Continued)

OTHER PUBLICATIONS

Berlin et al., "Excimer Laser Trabeculostomy: An Effective Microinvasive Glaucoma Surgery Procedure for Open-Angle Glaucoma", published Dec. 19, 2013 Third Party Submission in 010503.

(Continued)

*Primary Examiner* — Michael G Lee
*Assistant Examiner* — David Tardif
(74) *Attorney, Agent, or Firm* — Greenberg Traurig, LLP; David J. Dykeman; Roman Fayerberg (57) ABSTRACT

The invention provides an excimer laser system including a means for authenticating laser probes to be used with the excimer laser system via radio-frequency identification techniques.

21 Claims, 5 Drawing Sheets

(56) References Cited

U.S. PATENT DOCUMENTS

| | | |
|---|---|---|
| 7,443,296 B2 | 10/2008 | Mezhinsky et al. |
| 7,568,619 B2 | 8/2009 | Todd et al. |
| 7,801,271 B2 | 9/2010 | Gertner et al. |
| 9,489,785 B2 | 11/2016 | Klammer et al. |
| 9,642,746 B2 | 5/2017 | Berlin |
| 10,383,689 B2 | 8/2019 | Berlin |
| 11,076,933 B2 | 8/2021 | Junger et al. |
| 11,076,992 B2 | 8/2021 | Junger et al. |
| 11,103,382 B2 | 8/2021 | Junger et al. |
| 11,234,866 B2 | 2/2022 | Junger et al. |
| 11,389,239 B2 | 7/2022 | Junger et al. |
| 11,464,677 B2 | 10/2022 | Junger et al. |
| 11,529,260 B2 | 12/2022 | Junger et al. |
| 2002/0013572 A1 | 1/2002 | Berlin |
| 2002/0183726 A1 | 12/2002 | Elbrecht et al. |
| 2004/0082939 A1 | 4/2004 | Berlin |
| 2004/0114879 A1 | 6/2004 | Hiereth et al. |
| 2004/0147985 A1 | 7/2004 | MacFarland et al. |
| 2005/0192480 A1 | 9/2005 | Toriya et al. |
| 2005/0283148 A1 | 12/2005 | Janssen et al. |
| 2006/0111699 A1 | 5/2006 | Neuberger |
| 2006/0244652 A1* | 11/2006 | Tethrake ............... A61B 90/98 342/44 |
| 2007/0027443 A1 | 2/2007 | Rose et al. |
| 2007/0122096 A1 | 5/2007 | Temelkuran et al. |
| 2007/0147752 A1 | 6/2007 | Weisberg et al. |
| 2007/0219601 A1 | 9/2007 | Neuberger |
| 2007/0265602 A1 | 11/2007 | Mordaunt et al. |
| 2008/0054073 A1* | 3/2008 | Charles ............... A61B 90/90 235/385 |
| 2008/0082078 A1 | 4/2008 | Berlin |
| 2008/0097415 A1 | 4/2008 | Zimare et al. |
| 2008/0108981 A1 | 5/2008 | Telfair et al. |
| 2008/0108983 A1 | 5/2008 | Nadolski |
| 2008/0161781 A1 | 7/2008 | McArdle et al. |
| 2008/0269734 A1 | 10/2008 | Vila Echague et al. |
| 2009/0030300 A1 | 1/2009 | Hhaboussi et al. |
| 2009/0118715 A1 | 5/2009 | Mansour |
| 2009/0157064 A1* | 6/2009 | Hodel ............... A61B 90/90 235/441 |
| 2010/0019125 A1 | 1/2010 | Stefani et al. |
| 2010/0068141 A1 | 3/2010 | Kaushal et al. |
| 2010/0324543 A1 | 12/2010 | Kurtz et al. |
| 2011/0295243 A1 | 12/2011 | Peyman |
| 2011/0301507 A1 | 12/2011 | Romano et al. |
| 2012/0275481 A1 | 11/2012 | Riggs |
| 2013/0041357 A1* | 2/2013 | Neuberger ............... A61B 90/98 606/2 |
| 2013/0085484 A1 | 4/2013 | Van Valen et al. |
| 2014/0058367 A1 | 2/2014 | Dantus |
| 2014/0188076 A1 | 7/2014 | Chia et al. |
| 2014/0276603 A1 | 9/2014 | Magee et al. |
| 2014/0316388 A1 | 10/2014 | Hipsley |
| 2015/0051607 A1 | 2/2015 | Hajishah et al. |
| 2015/0080783 A1 | 3/2015 | Berlin |
| 2015/0148615 A1 | 5/2015 | Brennan et al. |
| 2015/0217133 A1 | 8/2015 | Angeley et al. |
| 2015/0297408 A1 | 10/2015 | Dolzan et al. |
| 2015/0305811 A1 | 10/2015 | Neuberger |
| 2015/0366706 A1 | 12/2015 | Belkin et al. |
| 2015/0374549 A1* | 12/2015 | Scott ............... A61F 9/013 606/5 |
| 2017/0100041 A1 | 4/2017 | Kasamatsu et al. |
| 2017/0202708 A1 | 7/2017 | Berlin |
| 2017/0304001 A1 | 10/2017 | Searle et al. |
| 2018/0000337 A1 | 1/2018 | Chen et al. |
| 2018/0042772 A1 | 2/2018 | Mansour |
| 2018/0263647 A1* | 9/2018 | Aljuri ............... A61B 8/12 |
| 2018/0271703 A1 | 9/2018 | Hallen |
| 2018/0303667 A1 | 10/2018 | Peyman |
| 2018/0353328 A1 | 12/2018 | Bacher et al. |
| 2018/0360310 A1 | 12/2018 | Berlin |
| 2019/0105200 A1 | 4/2019 | Hipsley |
| 2019/0117459 A1 | 4/2019 | Berlin |
| 2019/0262071 A1 | 8/2019 | Thom et al. |
| 2020/0078216 A1 | 3/2020 | Raksi |
| 2020/0078217 A1 | 3/2020 | Raksi |
| 2020/0330157 A1 | 10/2020 | Junger et al. |
| 2020/0330181 A1 | 10/2020 | Junger et al. |
| 2020/0330266 A1 | 10/2020 | Junger et al. |
| 2020/0330274 A1 | 10/2020 | Junger et al. |
| 2020/0330275 A1 | 10/2020 | Junger et al. |
| 2020/0330279 A1 | 10/2020 | Junger et al. |
| 2020/0330280 A1 | 10/2020 | Junger et al. |
| 2020/0330281 A1 | 10/2020 | Junger et al. |
| 2020/0390600 A1 | 12/2020 | Perera et al. |
| 2021/0235986 A1 | 8/2021 | Juhasz et al. |
| 2021/0259880 A1 | 8/2021 | Newton et al. |
| 2021/0298945 A1 | 9/2021 | Juhasz et al. |
| 2022/0022997 A1 | 1/2022 | Junger et al. |
| 2022/0023098 A1 | 1/2022 | Junger et al. |
| 2022/0031513 A1 | 2/2022 | Junger et al. |
| 2022/0151828 A1 | 5/2022 | Junger et al. |
| 2022/0183882 A1 | 6/2022 | Mosaed et al. |
| 2022/0183887 A1 | 6/2022 | Junger et al. |
| 2022/0280343 A1 | 9/2022 | Junger et al. |
| 2022/0387107 A1 | 12/2022 | Junger et al. |
| 2022/0387218 A1 | 12/2022 | Junger et al. |

FOREIGN PATENT DOCUMENTS

| | | |
|---|---|---|
| DE | 10138984 A1 | 3/2003 |
| EP | 1835862 B1 | 6/2011 |
| EP | 2120760 B1 | 9/2015 |
| WO | 2019060756 A1 | 3/2019 |
| WO | 2020215062 A1 | 10/2020 |
| WO | 2020215064 A1 | 10/2020 |
| WO | 2020215066 A1 | 10/2020 |
| WO | 2020215067 A1 | 10/2020 |
| WO | 2020215068 A1 | 10/2020 |
| WO | 2020215069 A1 | 10/2020 |
| WO | 2020215071 A1 | 10/2020 |
| WO | 20200215073 A1 | 10/2020 |

OTHER PUBLICATIONS

Dietlein et al., "Erbium: YAG Laser Trabecular Ablation (LTA) in the Surgical Treatment of Glaucoma", Lasers in Surgery and Medicine, Jan. 6, 1999, vol. 23, pp. 104-110.

ExTra Operating Instructions, Manufacturer: Mlase AG, published prior to Jan. 1, 2018.

Francis et al., "Combined Cataract Extraction and Trabeculotomy by the Internal Approach for Coexisting Cataract and Open-Angle Glaucoma: Initial Results", Journal of Cataract & Refractive Surgery, Jul. 1, 2008, vol. 34, pp. 1096-1103.

Investigation Testing Authorization Application, TUI Laser AG, Published Jan. 1, 2016.

Wilmsmeyer et al., "Excimer Laser Trabeculotomy: A New, Minimally Invasive Procedure for Patients With Glaucoma", Graefe's Archive for Clinical and Experimental Ophthalmology, Oct. 19, 2005, vol. 244, pp. 670-676.

Crandall, Alan, "Combining Cataract and Glaucoma Surgery", Review of Ophthalmology, 1-4, Jun. 13, 2008.

Grover, Davinder S. "When You Have Cataracts and Glaucoma", Glaucoma Research Foundation, Oct. 29, 2017.

Taliaferro, Kevin et al. "Excimer Laser Trabeculostomy Normalizing IOP and Restoring Physiologic Outflow in Glaucoma." Glaucoma Today, 2009, pp. 45-47 (Year: 2009).

Toteberg-Harms, et al., "Cataract surgery combined with excimer laser trabeculotomy to lower intraocular pressure: effectiveness dependent on preoperative IOP." BMC ophthalmology, vol. 13, No. 1, p. 24 (2013).

Tsai, James C. "High Eye Pressure and Glaucoma", Glaucoma Research Foundation, Oct. 29, 2017.

International Search Report in International Application No. PCT/US2020/028962 dated Jun. 2, 2020.

Leung et al., "Anterior Chamber Angle Measurement with Anterior Segment Optical Coherence Tomography: A Comparison between Slit Lamp OCT and Visante OCT" IOVS, pp. 3469-3474, Aug. 2008.

(56) References Cited

OTHER PUBLICATIONS

U.S. Appl. No. 16/389,404 US20200330275A1, filed Apr. 19, 2019 Oct. 22, 2020, Combination Treatment Using Phaco and ELT.
U.S. Appl. No. 16/389,437 US20200330281A1, filed Apr. 19, 2019 Oct. 22, 2020, Excimer Laser Fiber Illumination.
U.S. Appl. No. 16/389,359 US20200330279A1, filed Apr. 19, 2019 Oct. 22, 2020, Calibration System for Improving Manufacture Tolerance in Excimer Laser Optical Fibers.
U.S. Appl. No. 16/389,446 US20200330266A1, filed Apr. 19, 2019 Oct. 22, 2020, Combination Treatment Using ELT.
U.S. Appl. No. 16/389,460 US20200330274A1, filed Apr. 19, 2019 Oct. 22, 2020, Methods of Transverse Placement in ELT.
U.S. Appl. No. 16/389,425 US20200330280A1, filed Apr. 19, 2019 Oct. 22, 2020, Personalization of Excimer Laser Fibers.
U.S. Appl. No. 16/389,386 US20200330157A1, filed Apr. 19, 2019 Oct. 22, 2020, Enhances Fiber Probes for ELT.
MLase AG, ExTra Operating Instructions (Apr. 2016).†
MLase AG, Specifications FIDO Laser applicator for ExTra Laser system (Jul. 13, 2012).†
MLase AG, Specifications FIDO laser applicator for ExTra Laser System (Sep. 26, 2013).†
MLase AG, Specifications FIDO laser applicator for ExTra Laser System, dated Sep. 26, 2013.†
Investigation Testing Authorization Application, TUI Laser AG, 43 pages, published prior to Jan. 1, 2018.†

\* cited by examiner
† cited by third party

AUTHENTICATION SYSTEMS AND METHODS FOR AN EXCIMER LASER SYSTEM

CROSS REFERENCE TO RELATED APPLICATION

This application is a continuation patent application of U.S. application Ser. No. 16/389,346, filed Apr. 19, 2019, now granted as U.S. Pat. No. 11,076,933, the entire disclosure of which is hereby incorporated herein by reference.

TECHNICAL FIELD

The disclosure relates to medical devices, and, more particularly, to an excimer laser system including a means for authenticating probes to be used with the excimer laser system.

BACKGROUND

In the medical industry, there are many surgical devices, instruments and systems comprised of individual components that must work together properly to ensure treatment is performed safely and as intended. For example, medical laser systems are used to treat various conditions in various practice areas (i.e., urology, neurology, otorhinolaryngology, general anesthetic ophthalmology, dentistry, gastroenterology, cardiology, gynecology, and thoracic and orthopedic procedures). Medical laser systems consist of a laser unit, which generates laser radiation, and a separate laser probe having an optical fiber adapted to direct laser radiation from the laser, through the fiber and to the treatment area.

Specific components of a laser system can be designed by a manufacturer to be utilized with other specific components. For example, there are a variety of medical optical fibers available in the marketplace that can be used with laser systems. Currently available laser systems may provide laser light at various wavelengths and thus may be used for particular purposes and procedures. As such, optical fibers to be used with these laser systems may have varying sizes (diameter, length, etc.), be made of various materials, operate at various temperatures, operate at various wavelengths, and have physical characteristics (e.g., bend radii). Specific components of a laser system can be designed by a manufacturer to be utilized with other specific components. For example, there are many varieties of medical optical fibers available in the marketplace that can be used with laser systems that are used in medical procedures. Furthermore, the manufacturer of one component may also manufacture other components of a laser system, or may certify that these other components can be used with the manufacturer's own components.

Prior to beginning a medical procedure, it is important that the proper optical fiber be connected to the laser unit that is to be used for the medical procedure. Oftentimes, the manufacturer of the laser unit recommends usage of particular brands of optical fibers and/or particular optical fibers with the laser unit. When one of the components being used is not a certified product, the full capabilities of the system may not be achieved and may further cause malfunctions, endangering patient safety. For example use of an improper optical fiber can result in damage to the equipment, delay in conducting a medical procedure until the proper optical fiber is obtained, and/or result in the potential for an ineffective, damaging, or potentially life-threatening medical procedure.

SUMMARY

The present invention provides a system for authenticating laser probes for use with a laser system. In such a system, the elements generally include a laser unit and single-use, disposable laser probes to be coupled to the laser unit, each laser probe having an optical fiber adapted to direct laser radiation from the laser unit, through the fiber, and to the treatment area. The laser unit comprises a control system for operating the laser unit, including controlling output of laser radiation to a laser probe coupled to the laser unit. The laser unit further includes a means for authenticating any given laser probe to determine whether the laser probe is suitable and/or authorized to operate with the laser unit. In particular, the laser unit includes an RFID reader for reading data embedded in an RFID tag associated with the laser probe upon attachment of the laser probe to the laser unit. The data from the RFID tag is analyzed by the control system and a determination is made as to whether the laser probe is authentic (i.e., suitable for use with the laser unit). In the event that the laser probe is determined to be authentic, the control system allows for transmission of laser radiation to the laser probe and thus a procedure can be performed using the laser probe. In the event that the laser probe is determined to not be authentic, the control system prevents transmission of laser radiation to the laser probe.

The authentication analysis is based on a correlation of the RFID tag data with known, predefined authentication data stored in a database, either locally in the laser unit, or stored in a remote database. The known, predefined authentication data is controlled by the owner/manufacturer of the laser unit, such that the owner/manufacturer can determine what laser probes are to be used with the laser unit. The owner/manufacturer may set a specific authentication key or provide for specific identity numbers that are proprietary to the owner/manufacturer. As such, the RFID tag data for any given laser probe must include a corresponding unique identifier (i.e., authentication key or identity number) in order to be deemed authentic. The RFID tag data may include other information and/or characteristics associated with the laser probe and optical fiber. For example, in some embodiments, the RFID tag data further includes operational history information of the laser probe. As such, in some embodiments, it is further possible to utilize the control system to deauthenticate a laser probe based on operational history, such as in the event that the probe has already been used and/or reached the suggested maximum number of laser pulses, thereby preventing further use of the laser probe with the laser unit.

Accordingly, the authentication system of the present invention ensures that only authorized laser probes are able to be used with the laser unit. The authentication ensures that only those laser probes recommended and authorized by a manufacturer are to be used, thereby ensuring that the laser system functions as intended and patient safety is maintained. The authentication further protects against the use of counterfeit components. As counterfeit proprietary components become more prevalent, the need to authenticate original products becomes increasingly necessary. By embedding RFID directly into the laser probe and utilizing RFID technology for authentication, manufacturers can foil counterfeiters and secure recurring revenue streams, which may otherwise be lost due to counterfeit products.

DETAILED DESCRIPTION

The invention provides a system for authenticating laser probes for use with a laser system. In such a system, the elements generally include a laser unit and single-use, disposable laser probes to be coupled to the laser unit, each laser probe having an optical fiber adapted to direct laser radiation from the laser unit, through the fiber, and to the treatment area. The laser unit comprises a control system for operating the laser unit, including controlling output of laser radiation to a laser probe coupled to the laser unit. The laser unit further includes a means for authenticating any given laser probe to determine whether the laser probe is suitable and/or authorized to operate with the laser unit. In particular, the laser unit includes an RFID reader for reading data embedded in an RFID tag associated with the laser probe upon attachment of the laser probe to the laser unit. The data from the RFID tag is analyzed by the control system and a determination is made as to whether the laser probe is authentic (i.e., suitable for use with the laser unit). In the event that the laser probe is determined to be authentic, the control system allows for transmission of laser radiation to the laser probe and thus a procedure can be performed using the laser probe. In the event that the laser probe is determined to not be authentic, the control system prevents transmission of laser radiation to the laser probe.

Accordingly, the authentication system of the present invention ensures that only authorized laser probes are able to be used with the laser unit. The authentication ensures that only those laser probes recommended and authorized by a manufacturer are to be used, thereby ensuring that the laser system functions as intended and patient safety is maintained. The authentication further protects against the use of counterfeit components. As counterfeit proprietary components become more prevalent, the need to authenticate original products becomes increasingly necessary. By embedding RFID directly into the laser probe and utilizing RFID technology for authentication, manufacturers can foil counterfeiters and secure recurring revenue streams, which may otherwise be lost due to counterfeit products.

The laser unit and laser probe of the present invention is particularly well suited for intraocular procedures in which laser treatment of target tissues is desired. In particular, the laser probe and laser unit of the present invention is preferably used for treating glaucoma and useful in performing a laser trabeculostomy. However, it should be noted that a laser probe consistent with the present disclosure can be used in any laser treatment of various conditions, including other eye conditions (i.e., diabetic eye diseases, such as proliferative diabetic retinopathy or macular oedema, cases of age-related macular degeneration, retinal tears, and retinopathy of prematurity, and laser-assisted in situ keratomileusis (LASIK) to correct refractive errors, such as short-sightedness (myopia) or astigmatism) as well as other conditions in general and other practice areas (non-ocular practice areas).

Figure 1:
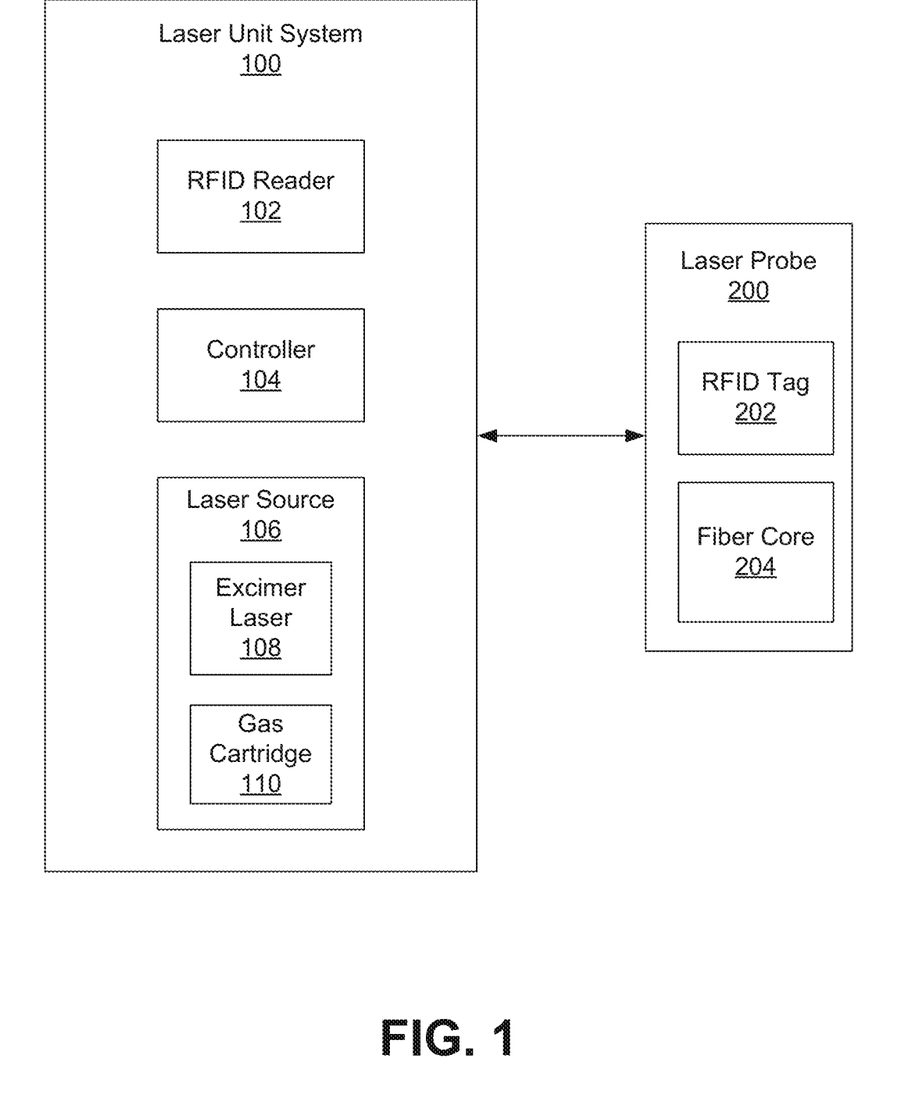
FIG. 1 diagrams an excimer laser system of the present disclosure.

FIG. 1 diagrams an excimer laser system, including a laser unit system 100 and a laser probe 200 to be attached to the laser unit system 100. The system 100 includes an RFID reader 102, a controller 104 (also referred to herein as a "control system 104"), and a laser source 108. The laser probe 200 includes an RFID tag 202 and a fiber core 204. As will be described in greater detail herein, many of the components of the laser unit system 100 may be contained in a housing, such as a moveable platform, to be provided in a setting in which the procedure is to be performed (e.g., operating room, procedure room, outpatient office setting, etc.) and the probe 200 may connect to the housing for use during treatment. Upon coupling the probe 200 to the housing, the fiber core 204 is coupled to the laser source 108 and adapted to direct laser radiation from the laser source 108, through the fiber, and to the treatment area.

The laser source 108 may include an excimer laser 110 and a gas cartridge 112 for providing the appropriate gas combination to the laser 110. The excimer laser 110 is a form of ultraviolet laser that generally operates in the UV spectral region and generates nanosecond pulses. The excimer gain medium (i.e., the medium contained within the gas cartridge 114) is generally a gas mixture containing a noble gas (e.g., argon, krypton, or xenon) and a reactive gas (e.g., fluorine or chlorine). Under the appropriate conditions of electrical stimulation and high pressure, a pseudo-molecule called an excimer (or in the case of noble gas halides, exciplex) is created, which can only exist in an energized state and can give rise to laser light in the UV range.

Laser action in an excimer molecule occurs because it has a bound (associative) excited state, but a repulsive (dissociative) ground state. Noble gases such as xenon and krypton are highly inert and do not usually form chemical compounds. However, when in an excited state (induced by electrical discharge or high-energy electron beams), they can form temporarily bound molecules with themselves (excimer) or with halogens (exciplex) such as fluorine and chlorine. The excited compound can release its excess energy by undergoing spontaneous or stimulated emission, resulting in a strongly repulsive ground state molecule which very quickly (on the order of a picosecond) dissociates back into two unbound atoms. This forms a population inversion. The excimer laser 110 of the present system 100 is an XeCl excimer laser and emits a wavelength of 308 nm.

The controller 104 provides an operator (i.e., surgeon or other medical professional) with control over the output of laser signals (from the laser source 108 to the fiber core 204) and, in turn, control over the transmission of laser energy from the fiber core 204 of the probe 200. However, prior to providing an operator with control over laser output, the laser probe 200 undergoes an authentication procedure to determine whether the laser probe 200 is in fact suitable for use with the laser unit system 100. In particular, upon coupling the laser prober 200 to the system 100, the RFID reader 102 reads data embedded in the RFID tag 202 of the laser probe 200, wherein such RFID tag data is analyzed to determine authenticity of the laser probe 200.

Figure 2:
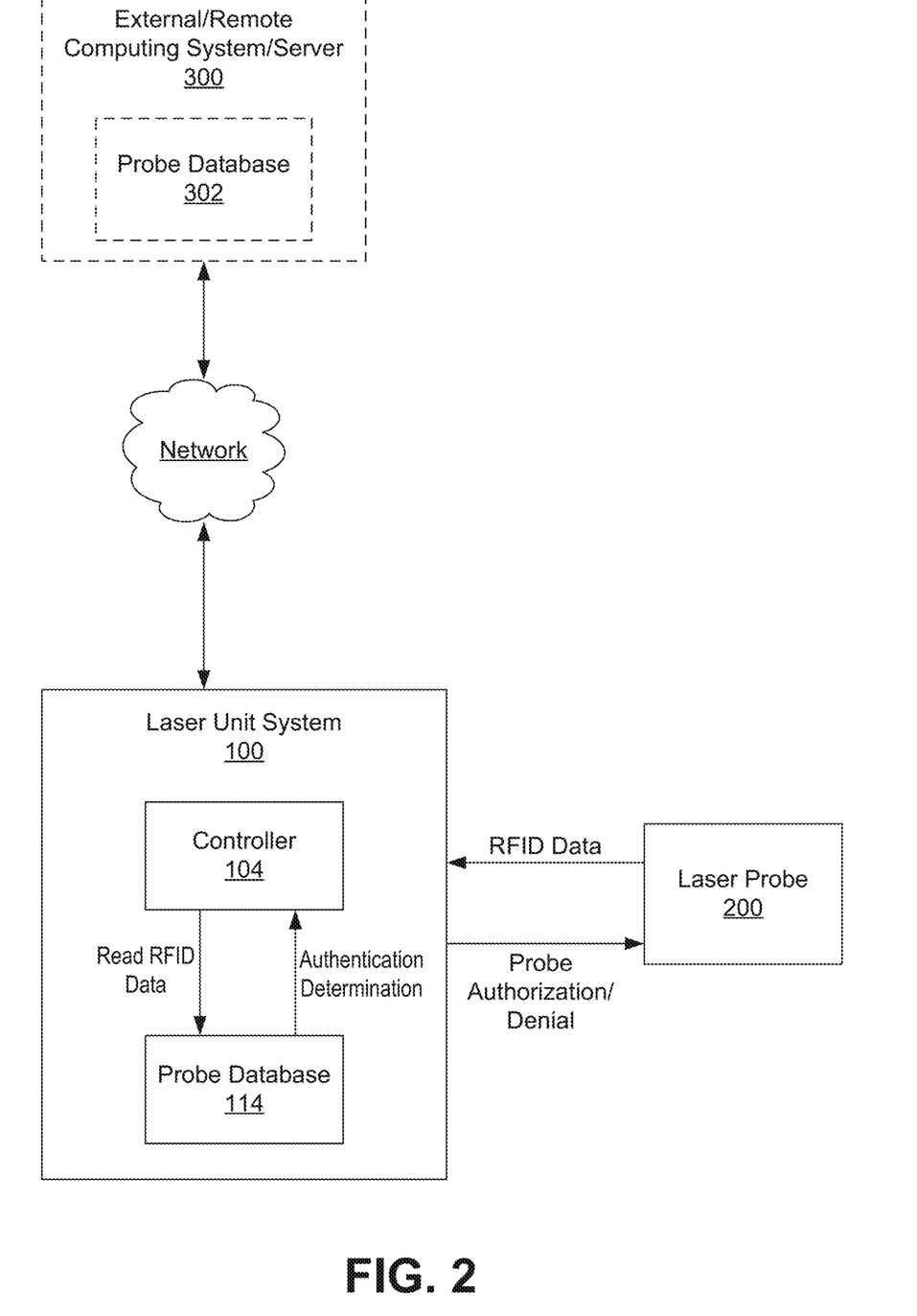
FIG. 2 diagrams the excimer laser system of the present disclosure and authentication of a laser probe to be used with the excimer laser system.

FIG. 2 diagrams the laser system 100 and authentication of a laser probe 200 to be used with the laser system 100. The data from the RFID tag is read by the RFID reader, and then analyzed by the controller 104. A determination is made as to whether the laser probe is authentic (i.e., suitable for use with the laser unit) based on the authentication analysis. In the event that the laser probe is determined to be authentic, the controller 104 allows for transmission of laser radiation to the laser probe 200 and thus a procedure can be performed using the laser probe 200. In the event that the laser probe is determined to not be authentic, the controller 104 prevents transmission of laser radiation to the laser probe 200.

The controller 104 may include software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. For example, the controller 104 may include a hardware processor coupled to non-transitory, computer-readable memory containing instructions executable by the processor to cause the controller to carry out various functions of the laser system 100 as described herein, including controller laser and/or illumination output.

The authentication analysis is based on a correlation of the RFID tag data with known, predefined authentication data stored in a database, either a local database (i.e., probe database 114) forming part of the laser unit system 100, or a remote database hosted via a remote server 300 (i.e., probe database 302). For example, in some embodiments, the system 100 may communicate and exchange data with a remote server 300 over a network. The network may represent, for example, a private or non-private local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web).

The known, predefined authentication data stored in the database (database 114 or database 302) may be controlled by the owner/manufacturer of the laser unit 100, for example, such that the owner/manufacturer can determine what laser probes are to be used with the laser unit. For example, the owner/manufacturer may set a specific authentication key or provide for specific identity numbers that are proprietary to the owner/manufacturer. As such, the RFID tag data for any given laser probe must include a corresponding unique identifier (i.e., authentication key or identity number) in order to be deemed authentic.

One approach to uniquely identifying a laser probe is to authenticate the probe by using a private key. In such an approach, both the laser system 100 and the RFID tag 202 are taught an identical key. The RFID tag 202 and laser system 100 then operate in conjunction to authenticate the key. More specifically, the laser system 100 generates a random, unique challenge number. The RFID tag 202 uses this challenge, in combination with the key to generate a response of an authentication code. The method for generating this code (known as a hash function) masks the value of the key. Another approach to uniquely identifying a laser probe is to use unique and unchangeable identity numbers. This approach can be used if there is a region of memory (e.g., a serial or model number), that can only be written by the RFID manufacturer. The protection is realized by ensuring that the manufacturer only provides tags with legal identification numbers, which prevents simple duplication of legitimate tags.

The RFID tag data may include other information and/or characteristics associated with the laser probe and optical fiber. For example, in some embodiments, the RFID tag data further includes operational history information of the laser probe. As such, in some embodiments, it is further possible to utilize the controller 104 to deauthenticate a laser probe based on operational history, such as in the event that the probe has already been used and/or reached the suggested maximum number of laser pulses, thereby preventing further use of the laser probe with the laser unit.

As generally understood, RFID technology uses electromagnetic fields to automatically identify and track tags attached to objects. As previously noted, the RFID tag associated with the laser probe contains electronically-stored information. The RFID tag may either be read-only, having a factory-assigned serial number that is used as a key into a database, or may be read/write, where object-specific data can be written into the tag by the system user. Field programmable tags may be write-once, read-multiple; "blank" tags may be written with an electronic product code by the user. The RFID tag contains at least three parts: an integrated circuit that stores and processes information and that modulates and demodulates radio-frequency (RF) signals; a means of collecting DC power from the incident reader signal; and an antenna for receiving and transmitting the signal. The tag information is stored in a non-volatile memory. The RFID tag includes either fixed or programmable logic for processing the transmission and sensor data, respectively.

The RFID reader transmits an encoded radio signal to interrogate the tag. The RFID tag receives the message and then responds with its identification and other information. This may be only a unique tag serial number, or may be product-related information such as a stock number, lot or batch number, production date, or other specific information. Since tags have individual serial numbers, the RFID system design can discriminate among several tags that might be within the range of the RFID reader and read them simultaneously.

In some embodiments, the RFID tag may be a passive tag, which collects energy from the RFID reader of the laser system interrogating radio waves. In some embodiments, the RFID tag may be an active tag, which includes a local power source (e.g., a battery) and may operate hundreds of meters from the RFID reader of the laser system.

Figure 3:
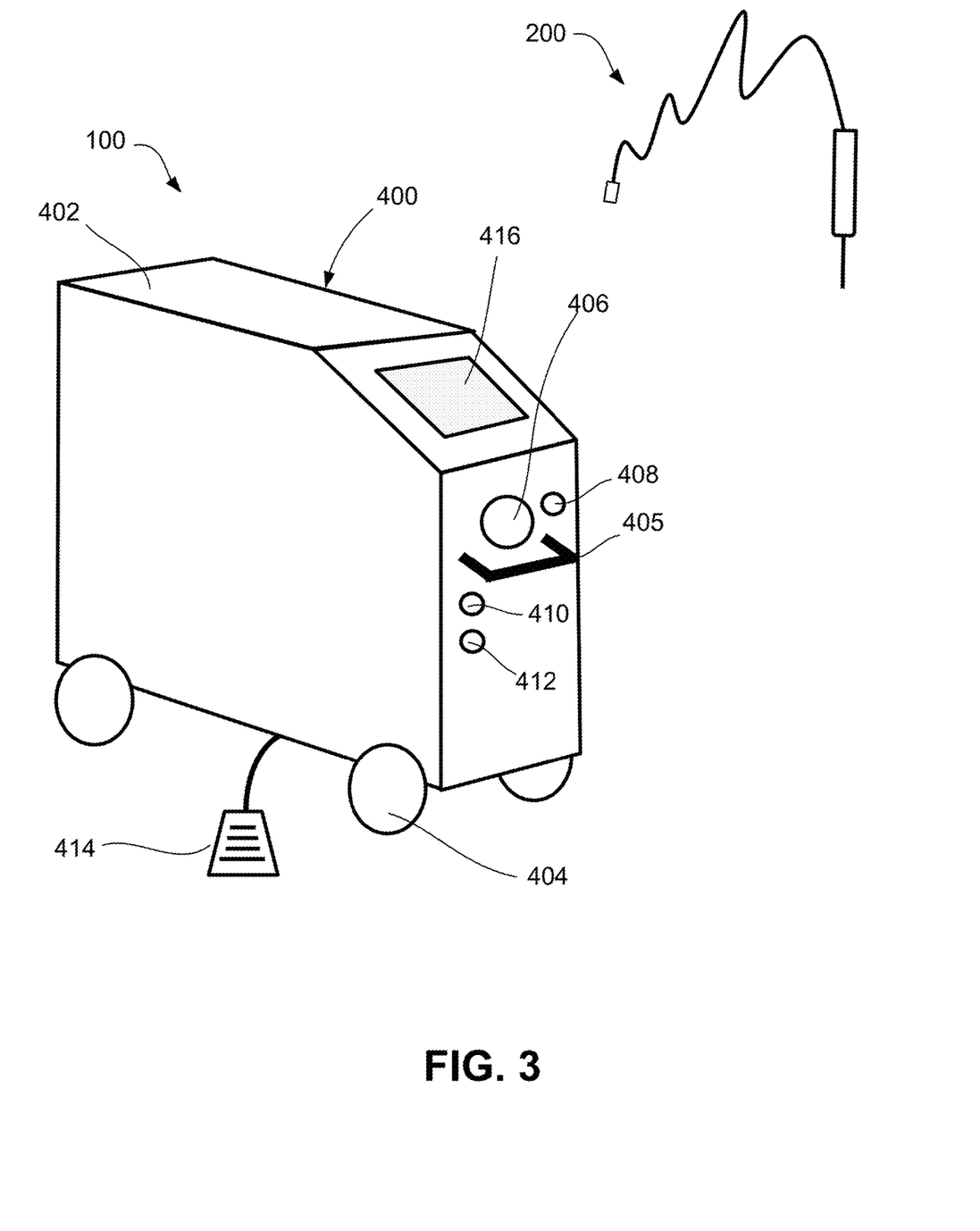
FIG. 3 shows an embodiment an excimer laser unit.

FIG. 3 shows an embodiment an excimer laser unit 100 provided in an instrument 400. As previously described, one or more components of the system 100 can be contained within the instrument 400. In the present embodiment, the RFID reader 102, controller 104, and laser source 108 (including the excimer laser 110 and gas cartridge 112) are contained within a housing 402. The housing 402 has wheels 404 and is portable. The instrument 400 further includes a push-pull handle 405 which assists with portability of the instrument 400. The instrument 400 further includes a connection port 406 for receiving a connecting end of the laser probe 200 to establish a connection between the fiber core 204 and the laser source 108. It should further be noted that the RFID reader 102 may be located in proximity to the connection port 406 to allow reading of data from the RFID tag 202 that is provided on a connecting end of the laser probe 200. The instrument 400 further includes various inputs for the operator, such as fiber probe cap holder 408, an emergency stop button 410, and a power switch 412. The instrument 400 further includes a foot pedal 414 extending from the housing 402 and is operable to provide control over the delivery of shots from the excimer laser 410 to the fiber core 204 of the probe 200. The instrument 400 further includes a display 416, which may be in the form of an interactive user interface. In some examples, the interactive user interface displays patient information, machine settings, and procedure information.

Figure 4:
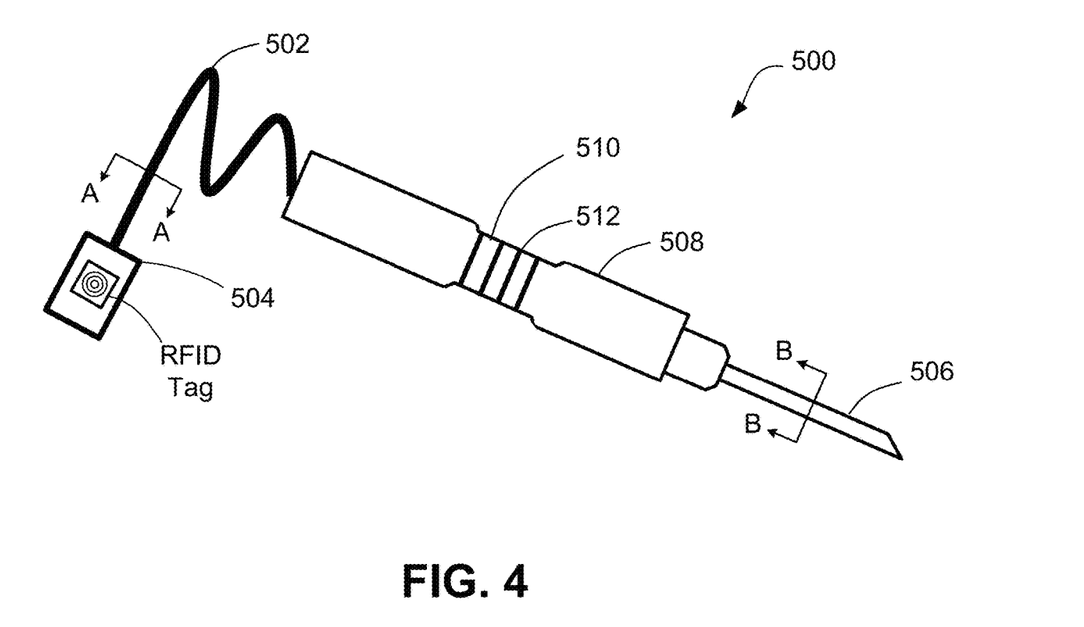
FIG. 4 shows an embodiment of a probe for use with the excimer laser system.

FIG. 4 shows an embodiment of a probe 500 for use with the excimer laser system 100. The probe 500 is a single use, disposable unit. The probe 500 generally includes a fiber core coupled to the laser source 108 by way of a connector 502 (elongated cord) extending from the body of the probe 500 and having a connection assembly 504 configured to be received within the connection port 406 of the instrument 400. The RFID tag 202 is provided on the connection assembly 504, such that, upon coupling the connection assembly 504 to the connection port 406 of the laser unit system 100, data embedded in the RFID tag 202 can be read by the RFID reader 102. The probe 500 further includes a delivery tip 506 from which laser energy (from the fiber core) may be emitted. The probe 500 includes a handheld body 508, which may include a finger grip 510 with ridges or depressions 512. The body 508 of the handheld probe 500 may be metal or plastic.

Figure 5:
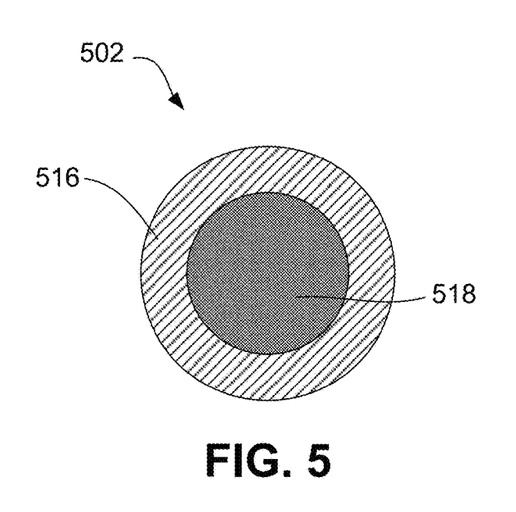
FIG. 5 shows a cross-sectional view of the probe taken along line A-A of FIG. 4.
Figure 6:
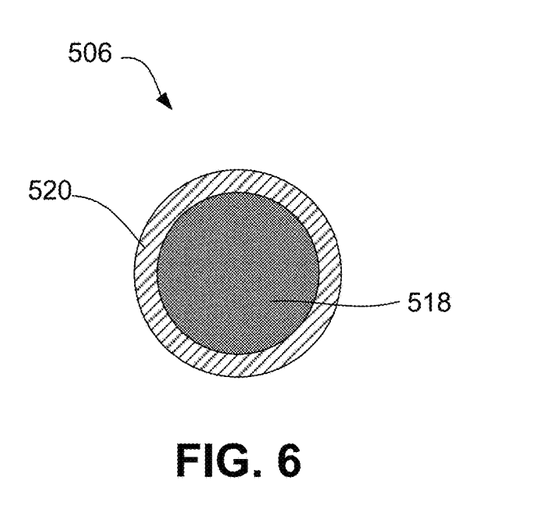
FIG. 6 shows a cross-sectional view of the probe taken along line B-B of FIG. 4.

FIGS. 5 and 6 show cross-sectional views of the probe 500 taken along line A-A and line B-B of FIG. 4, respectively. As shown, a fiber optic core 518 runs through the probe 500 and forms part of the connector 502. A protective sheath 516 surrounds the fiber optic core 518. In some examples, the protective sheath 516 is a protective plastic or rubber sheath. The fiber optic core 518 further form part of the delivery tip 506 of the probe 500. A metal jacket 520 surrounds the fiber optic core 518 and optical fiber 520. In some instances, a stainless steel jacket 520 surrounds and protects the fiber optic core 518.

Figure 7:
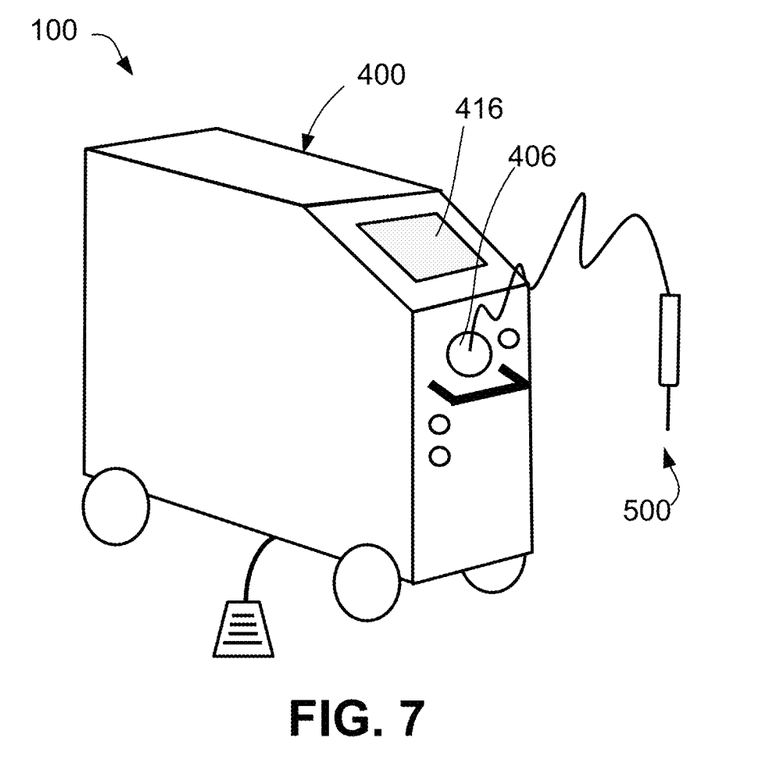
FIG. 7 shows an embodiment a laser probe attached to an excimer laser unit.
Figure 8:
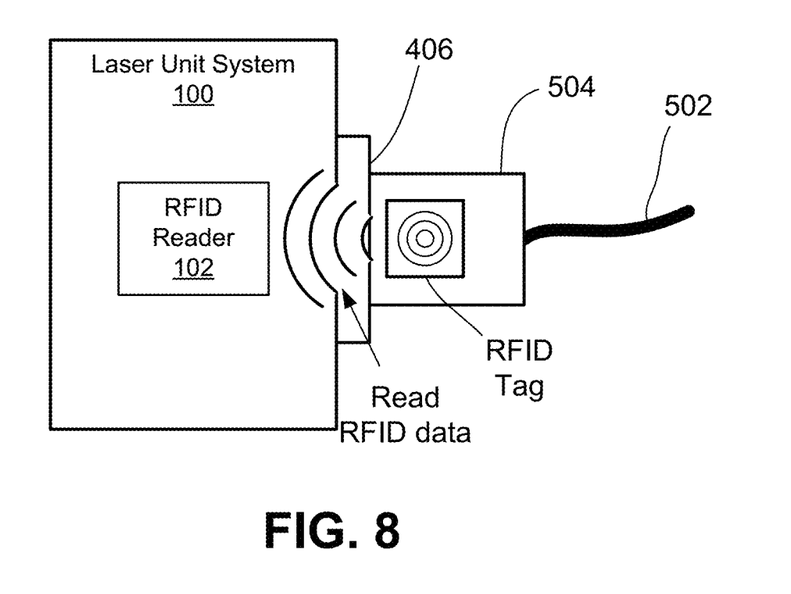
FIG. 8 shows an enlarged view of a connection between the laser probe and the excimer unit and initial RFID reading to determine authenticity of the laser probe.

FIG. 7 shows an embodiment a laser probe 500 attached to a laser unit system 100. As previously described, upon attachment of the laser probe 500 to the system 100 (i.e., coupling between the connection assembly 504 of the probe 500 and connection port 406 of the system 400), the RFID reader 102 reads data embedded in the RFID tag associated with connection assembly 504. FIG. 8 shows an enlarged view of a connection between the laser probe 500 and the system 100 and initial RFID reading to determine authenticity of the laser probe 200. The data from the RFID tag is analyzed by the controller 104 and a determination is made as to whether the laser probe is authentic (i.e., suitable for use with the laser unit). In the event that the laser probe 200 is determined to be authentic, the controller allows for transmission of laser radiation to the laser probe 200. In the event that the laser probe 200 is determined to not be authentic, the controller 104 prevents transmission of laser radiation to the laser probe.

Accordingly, the authentication system of the present invention ensures that only authorized laser probes are able to be used with the laser unit. The authentication ensures that only those laser probes recommended and authorized by a manufacturer are to be used, thereby ensuring that the laser system functions as intended and patient safety is maintained. The authentication further protects against the use of counterfeit components. As counterfeit proprietary components become more prevalent, the need to authenticate original products becomes increasingly necessary. By embedding RFID directly into the laser probe and utilizing RFID technology for authentication, manufacturers can foil counterfeiters and secure recurring revenue streams, which may otherwise be lost due to counterfeit products.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A laser probe for use in treating an eye condition, said laser probe comprising:
    a fiber optic core;
    a jacket surrounding the fiber optic core;
    a rigid handheld component positioned around an exterior of the jacket, wherein the rigid handheld component has a larger diameter than a diameter of the jacket surrounding the fiber optic core;
    a delivery tip extending from a distal portion of the rigid handheld component, wherein the delivery tip is configured to be manipulated by a user via movement of a hand of the user while the hand of the user grasps the rigid handheld component;
    a connector extending from a proximal portion of the rigid handheld component, the connector attachable to a laser unit comprising an excimer laser source; and
    a radio-frequency identification (RFID) tag associated with the connector, the RFID tag comprising data associated with a unique identifier of the laser probe, wherein:
        an RFID reader of the laser unit is configured to read the data from the RFID tag while the connector is attached to a connection port of the laser unit; and
        a controller of the laser unit is configured to activate or deny use of the excimer laser source with the laser probe based on a determination by the controller, based at least in part on the data from the RFID tag, that the laser probe is compatible for use with the laser unit.

2. The laser probe of claim 1, wherein the laser probe is a disposable, single-use probe.

3. The laser probe of claim 1, wherein the RFID tag comprises a passive RFID tag.

4. The laser probe of claim 3, wherein the passive RFID tag provides data in response to electromagnetic energy emitted from said RFID reader.

5. The laser probe of claim 1, wherein the RFID tag comprises an active RFID tag.

6. The laser probe of claim 5, wherein the active RFID tag periodically broadcasts signals, including the data, to be received by the RFID reader.

7. The laser probe of claim 1, wherein the controller is configured to correlate the unique identifier to authentication data, wherein:
    the controller is configured to activate use of the excimer laser source upon a positive correlation between the unique identifier and the authentication data, and
    the controller is configured to deny use of the excimer laser source upon a negative correlation between the unique identifier and the authentication data.

8. The laser probe of claim 1, wherein the data further comprises operational history data of the laser probe.

9. The laser probe of claim 8, wherein the operational history data is indicative of whether the laser probe has been previously used or that the laser first probe has been used for a predetermined number of pulses.

10. The laser probe of claim 1, wherein the RFID tag is configured to be deauthenticated by the controller of the laser probe after use of the laser probe such that, after the deauthentication, the controller of the laser unit or another laser unit is configured to deny use of the excimer laser source with the laser probe.

11. The laser probe of claim 10, wherein the deauthentication occurs after the laser probe is used for a predetermined maximum number of pulses.

12. The laser probe of claim 1, wherein the determination that the laser probe is compatible for use with the laser unit further comprises determining, based on the data from the RFID tag, whether the laser probe has been previously deauthenticated.

13. The laser probe of claim 1, wherein the delivery tip is insertable into an incision in an eye of a patient during performance of an excimer laser trabeculostomy on the eye of the patient.

14. A laser probe comprising:
    a fiber optic core;
    a jacket surrounding the fiber optic core;
    a rigid handheld component positioned around an exterior of the jacket, wherein the rigid handheld component has a larger diameter than a diameter of the jacket surrounding the fiber optic core;
    a delivery tip extending from a distal portion of the rigid handheld component, wherein the delivery tip is configured to be manipulated by a user via movement of a hand of the user while the hand of the user grasps the rigid handheld component;
    a connector extending from a proximal portion of the rigid handheld component, the connector attachable to a laser unit comprising an excimer laser source; and
    a radio-frequency identification (RFID) tag associated with the connector, the RFID tag comprising data associated with a unique identifier of the laser probe, wherein:

the data further comprises an indication that the laser probe has been previously used with the laser unit or another laser unit;

an RFID reader of the laser unit is configured to read the data from the RFID tag while the connector is attached to a connection port of the laser unit; and a controller of the laser unit is configured to deny use of the excimer laser source with the laser probe based on the indication that the laser probe has been previously used with the laser unit or another laser unit.

15. The laser probe of claim 14, wherein the indication that the laser probe has been previously used with the laser unit or another laser unit is part of operational history data stored on the RFID tag.

16. The laser probe of claim 14, wherein the laser probe is a disposable, single-use probe.

17. The laser probe of claim 14, wherein the indication that the laser probe has been previously used with the laser unit or another laser unit further indicates that the laser probe has been used for a predetermined maximum number of pulses.

18. A laser probe comprising:

a fiber optic core;

a jacket surrounding the fiber optic core;

a rigid handheld component positioned around an exterior of the jacket, wherein the rigid handheld component has a larger diameter than a diameter of the jacket surrounding the fiber optic core;

a delivery tip extending from a distal portion of the rigid handheld component, wherein the delivery tip is configured to be manipulated by a user via movement of a hand of the user while the hand of the user grasps the rigid handheld component;

a connector extending from a proximal portion of the rigid handheld component, the connector attachable to a laser unit comprising an excimer laser source; and a radio-frequency identification (RFID) tag associated with the connector, the RFID tag comprising data associated with a unique identifier of the laser probe, wherein:

an RFID reader of the laser unit is configured to read the data from the RFID tag while the connector is attached to a connection port of the laser unit; and a controller of the laser unit is configured to activate use of the excimer laser source with the laser probe based on a positive correlation between the unique identifier and authentication data.

19. The laser probe of claim 18, wherein the authentication data is stored on memory in the laser unit.

20. The laser probe of claim 18, wherein the authentication data is stored on memory of an external computing device that is separate from the laser unit.

21. The laser probe of claim 20, wherein the controller of the laser unit is configured to communicate with the external computing device over a network to determine the positive correlation.

* * * * *